United States Patent [19]

Hickok et al.

[11] Patent Number: 5,269,683
[45] Date of Patent: Dec. 14, 1993

[54] MIRROR FOR MICROSCOPIC ENDODONTIC EXAMINATION

[76] Inventors: Teresa R. Hickok, 730 "B" Edgewater Dr.; Claude E. Martin, 2039 #104 Lakeridge Cir., both of Chula Vista, Calif. 91913

[21] Appl. No.: 885,143
[22] Filed: May 18, 1992
[51] Int. Cl.⁵ .......................... A61B 1/24; G02B 5/08; G02B 7/182
[52] U.S. Cl. ...................... 433/30; 359/838; 359/871; 359/882
[58] Field of Search ........................ 359/838, 872, 882; 433/30, 31; 128/10, 11

[56] References Cited

U.S. PATENT DOCUMENTS

| | | | |
|---|---|---|---|
| 224,663 | 2/1880 | Donaldson | 433/30 |
| D. 231,737 | 6/1974 | Tanner | D24/1 D |
| D. 236,727 | 9/1975 | Tanner | D24/1 D |
| D. 238,281 | 12/1975 | Cali | D24/1 D |
| 1,054,488 | 2/1913 | Bailey | 433/31 |
| 1,509,041 | 9/1924 | Hyams | 433/31 |
| 2,534,706 | 12/1950 | Gittelson | 359/882 |
| 2,627,206 | 2/1953 | Clark | 359/882 |
| 2,686,456 | 8/1954 | Szuba et al. | 359/882 |
| 3,164,904 | 1/1965 | Barnes | 433/30 |
| 3,638,013 | 1/1972 | Keller | 240/41.15 |
| 4,074,416 | 2/1978 | Rambauske et al. | 82/12 |
| 4,090,506 | 5/1978 | Pilgrim | 128/11 |
| 4,629,425 | 12/1986 | Detsch | 433/31 |
| 5,087,279 | 2/1992 | Monji et al. | 65/64 |

*Primary Examiner*—Bruce Y. Arnold
*Assistant Examiner*—John Juba, Jr.
*Attorney, Agent, or Firm*—Baker, Maxham, Jester & Meador

[57] ABSTRACT

A precision hand mirror for use in endodontic examinations for viewing the interior of small cavities. The mirror is suitable for use with a microscope but is not limited to such use. The materials and method of fabrication make this mirror suitable for heating in an autoclave at temperatures up to 450° C. A tungsten-carbide mirror blank is polished to reduce surface roughness to less than five percent of the wavelength of visible light, thereby removing all distortion from microscopic examination at any magnification. The tightly-packed crystalline structure of the C-2 tungsten-carbide material used in the mirror is highly resistant to physical distortion and corrosion problems normally resulting from repeated autoclave heating and exposure to bodily fluids during endodontic examinations.

16 Claims, 3 Drawing Sheets

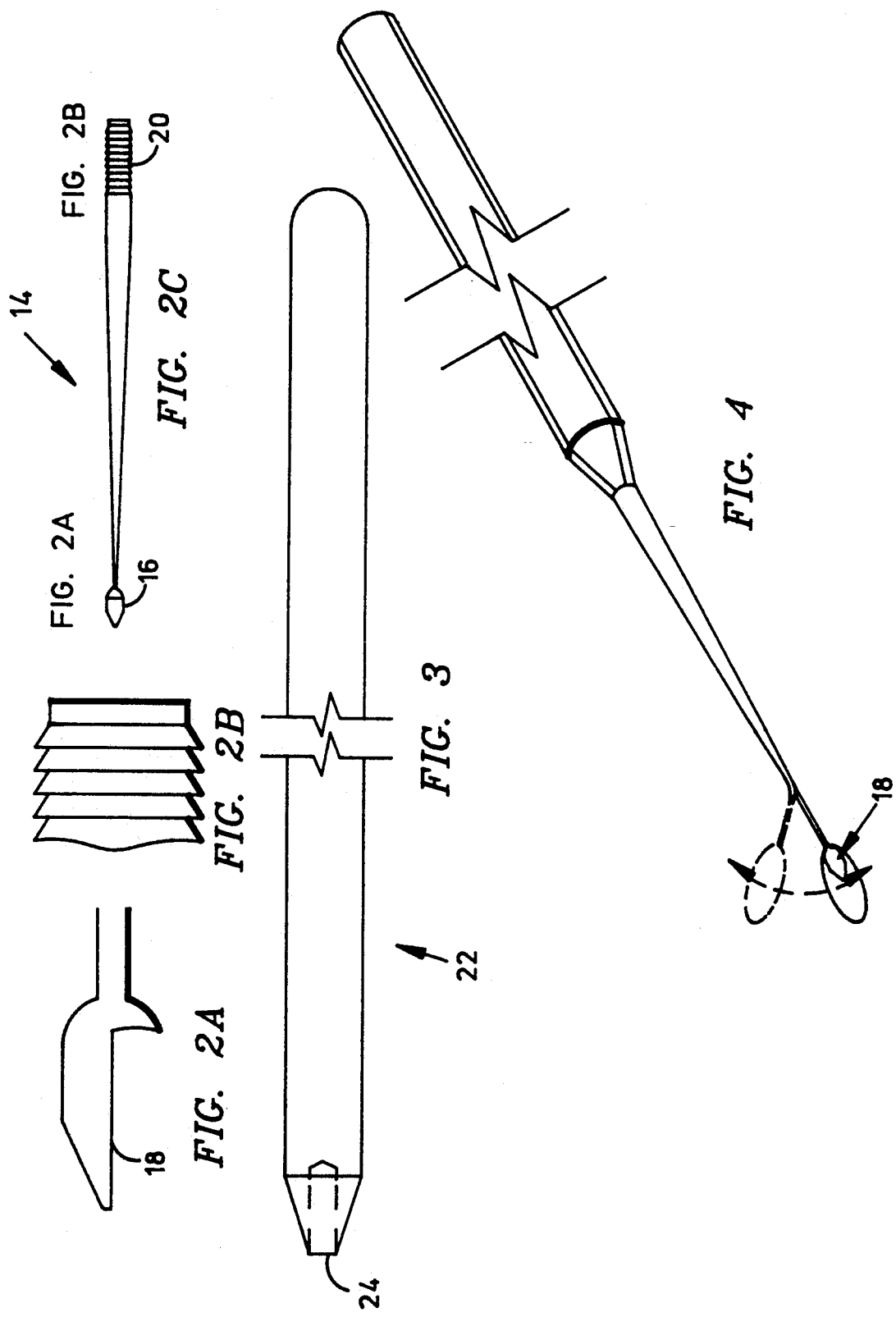

MIRROR FOR MICROSCOPIC ENDODONTIC EXAMINATION

BACKGROUND OF THE INVENTION

1. Field of the Invention

Our invention relates generally to dental examination mirrors and, more specifically, to a small, highly-reflective mirror for the microscopic survey of the interior of small cavities such as the pulp region of a human tooth.

2. Discussion of the Related Art

The use of hand mirrors for dental examinations has been known for at least a century. The typical dental hand mirror known in the art employs a glass plate with a reflective coating deposited on one side together with a handle and perhaps some form of adjustable neck. Such devices are suitable for examining the interior of the mouth and the surfaces of the teeth but are usually too large for use in examining the tooth interior except that portion visible from the exterior of the tooth.

A variety of inventive means for illumination, cleaning and positioning of dental examination mirrors have been proposed over the years by practitioners in the art. For instance, in U.S. Pat. No. 1,509,041, H. T. Hyams, discloses a dental appliance which combines a source of light, an adjustable mirror, and an optical viewing apparatus for examination of the interior of the mouth. In U.S. Pat. No. 3,368,013, the inventor discloses a dental mirror that is used with a fiber optic cable or the like for illumination. Also, in U.S. Pat. No. 4,629,425, S. G. Detsch discloses a dental mirror apparatus with integral means for delivery of pressurized air, water or combination thereof to the mirror surface for cleaning. However, none of these practitioners teach or suggest a dental mirror apparatus suitable for the examination of the interior of a tooth such as is desired during endodontic procedures.

The fundamental problems presented by the typical endodontic procedure are the small size of the interior work space, the high levels of (corrosive) body fluids generated during such procedures and the requirement for some form of distortion-free optical magnification. The typical glass dental mirror is too large to permit partial insertion into the endodontic cavity. It also is not optically suitable for use with microscopic examination equipment because the glass surface is generally insufficiently flat to avoid optical distortion of a magnified image.

The size problem can be readily corrected by using a very small reflective surface. However, a glass mirror manufactured in a very small size does not resolve either of the remaining two problems In fact, very small glass reflective surfaces tend to introduce distortion under magnification and cannot be readily bonded to the mirror neck without loss of optical flatness.

The fragility and distortion problems of small glass reflectors can be overcome by substituting a polished metal surface for the glass reflector. However, the corrosive effects of the bodily fluids generated during endodontic procedures and the repeated autoclave heating imposed on dental implements will rapidly destroy the surface polish on metallic reflectors. Practitioners in the art have suggested various solutions to these problems but none of the suggestions have properly resolved all three problems simultaneously, until now.

There is a clearly felt need in the endodontic art for a hand mirror that is suitable for use in examining the interior of the tooth under magnification without significant optical distortion. Such a mirror must also be suitable for heating to autoclave temperatures without loss of optical properties. These unresolved problems and deficiencies are clearly felt in the art and are solved by our invention in the manner described below.

SUMMARY OF THE INVENTION

The endodontic mirror of our invention includes a highly polished non-metallic reflecting surface that is sufficiently stable during temperature cycling to avoid physical distortion and corrosion from exposure to bodily fluids and autoclave heating. For this reflecting surface, we use type C-2 tungsten-carbide (written chemically as "WC"), which is a very hard, fine-grain mineral compound that is not readily subject to corrosion or physical deformation.

Our reflecting surface can be manufactured in any size or shape down to a very small size, thereby permitting the user to insert a significant portion of reflecting surface into the pulp region of a tooth by way of a canal created according to normal endodontic practice. The reflecting surface of our invention is bonded to a flexible wire neck with silver solder, thereby avoiding any requirement for the bulky holding elements normally required for glass reflectors.

The tungsten-carbide reflecting surface is polished to reduce roughness to 25 nanometers rms, which is less than five percent of the wavelength of visible light. This high polish ensures distortion-free viewing at any level of magnification.

It is an object of our invention to provide a mirror suitable for viewing the interior region of a human tooth during endodontic procedures. It is another object of our invention to provide a dental mirror suitable for distortion-free high-magnification examinations of any sort. It is yet another object of our invention to provide a dental mirror that can withstand the corrosive effects of bodily fluids and autoclave temperatures up to 450° C. without significant deterioration of optical properties.

It is yet also an object of our invention to provide a hand mirror with a flexible neck element that can be repositioned conveniently but only upon application of relatively high repositioning forces. It is an advantage of our invention that the stainless-steel wire neck is very stable and yet can be bent dozens of times to reposition the reflector without metal fatigue.

The foregoing, together with other objects, features and advantages of our invention, will become more apparent when referring to the following specification, claims and the accompanying drawing.

BRIEF DESCRIPTION OF THE DRAWING

For a more complete understanding of our invention, we now refer to the following detailed description of the embodiments as illustrated in the accompanying drawing, wherein:

FIG. 2, comprising FIGS. 2A–2B, shows the preferred embodiment of the stainless-steel alloy neck wire of our invention;

FIG. 3 shows an illustrative embodiment of the handle element of our invention;

FIG. 4 shows an oblique view of an illustrative embodiment of the assembled mirror of our invention.

DETAILED DESCRIPTION OF THE PREFERRED EMBODIMENTS

Figures 1A, 1B, 1C:
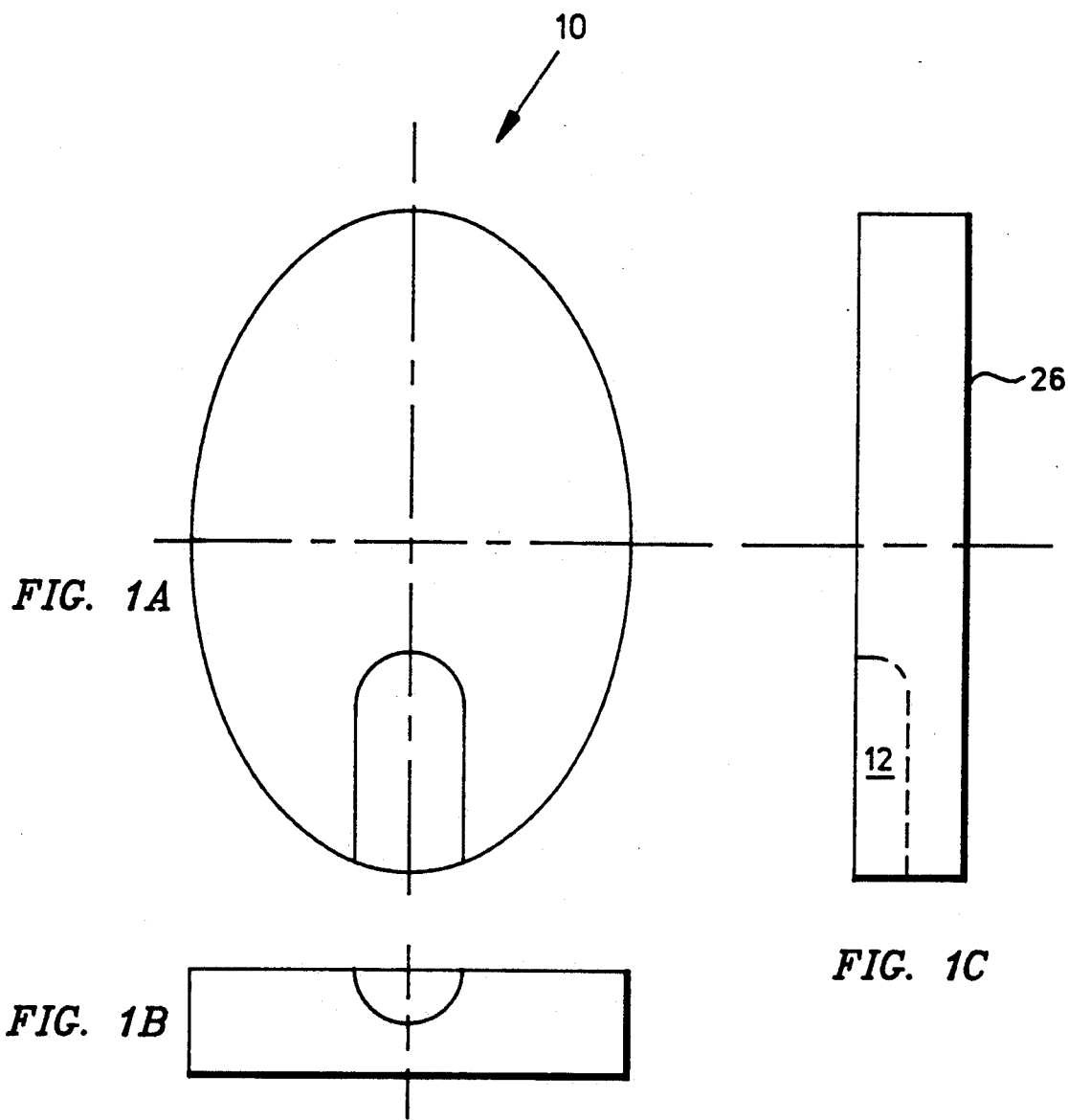
FIG. 1 shows a three-view specification drawing for the preferred embodiment of the tungsten-carbide mirror blank of our invention.

FIG. 1 shows a three-view specification drawing of the tungsten-carbide mirror blank 10. We prefer to cut mirror blank 10 from round rod stock (not shown) having a diameter equal to the dimension "A" shown in FIG. 1. By appropriate adjustment of the angle at which blank 10 is cut from the rod stock, the dimension "B" shown in FIG. 1 can be varied to provide a variety of sizes. Three preferred sizes for mirror blank 10 are illustrated in FIG. 1.

Mirror blank 10 can be used without additional cutting but we prefer to cut a small channel 12 for insertion and registration of the flexible neck 14 illustrated in FIG. 2. The thickness of blank 10 must be sufficient to permit the cutting of channel 12 without loss of strength. We have experimented with thicknesses for blank 10 of 0.3 to 0.5 millimeters without cutting channel 12, but we prefer to retain a minimum thickness of 0.6 millimeters as a provision against chipping or shattering during normal use. Thus, FIG. 1 shows a minimum thickness of 0.635 millimeters at the bottom of channel 12.

We also prefer the elliptical shape shown for mirror blank 10 because it is easy to slice from round bar stock and can be made sufficiently long and narrow to permit insertion of a portion of the reflective surface into a small endodontic channel or cavity.

FIG. 2, comprising FIGS. 2A-2B, shows the preferred embodiment of flexible neck 14. We use a 303 CRES stainless-steel alloy wire to form neck 14 because of its resistance to fatigue failure and its compatibility with the 50-50 silver solder used to bond with the tungsten-carbide mirror blank 10 of FIG. 1. We machine the initial wire stock as shown to provide a taper, leaving a narrow head end 16 as shown in FIG. 2B adapted to fit into channel 12 in FIG. 1. The solder bond area 18 is illustrated in FIG. 4.

If a mirror blank is used without channel 12, end 16 can be flattened to a larger surface area for bonding with silver solder.

The tail end 20 of neck 14 is machined to form a series of grooves as illustrated in more detail in FIG. 2A. These grooves are provided to permit insertion of neck 14 into handle 22 at the tip 24 shown in FIG. 3. Because handle 22 is made of a softer metal alloy than neck 14, tail end 20 can be compression-fitted into tip 24 and will remain securely positioned because of the toothed configuration of tail end 20 shown in FIG. 2A.

The tapered region of neck 14 is made sufficiently small to permit neck 14 to be bent in any direction by applying force at head end 16. For the preferred stainless-steel alloy 303 CRES with a taper over a 30 millimeter length from about 2.3 millimeters diameter to slightly less than 1.0 millimeters diameter, a lateral force of over 4 newtons at head end 16 is required to bend neck 14. This high stiffness combined with good flexibility is very useful, permitting the user to push and prod firmly with the mirror without losing the desired position that was initially set by the user.

FIG. 4 shows an oblique view of the mirror of this invention with neck 14 fitted into handle 22 and mirror blank 10 bonded to head end 16 with silver solder at bond area 18.

Figure 5:
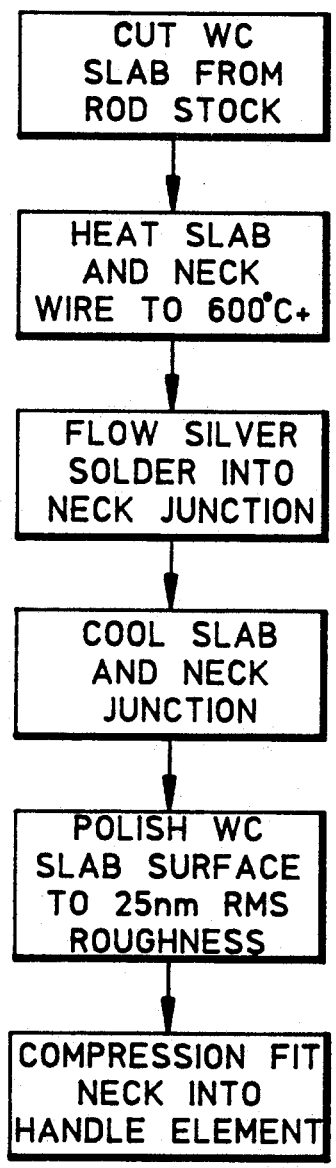
FIG. 5 provides a flow chart illustrating the fabrication method of our invention.

FIG. 5 is a flow chart illustrating the fabrication and polishing steps of the method of our invention. The sequence of these steps is important because the silver soldering process requires temperatures high enough to distort a polished mirror surface 26. Accordingly, we prefer heating blank 10 and head end 16 in the presence of silver solder until the solder has flowed to fill the bonding region 28 (FIG. 4). After flowing the solder in bond region 28, the assembly is cooled to permit cure of the silver solder bond. Finally, after cure of the silver solder bond, surface 26 is polished in accordance with our preferred series of polishing steps.

Handle 22 in FIG. 3 can be any suitable material capable of withstanding autoclave temperatures up to 450° C. but we prefer the relatively soft 2024 T-4 aluminum alloy with an anodized coating. This is an inexpensive durable light handle that can be produced in a variety of colors for ease of identification. Identification by color is an important consideration for dental and surgical tools and the availability of various anodizing colors meets this requirement.

The preferred polishing technique is a four-stage diamond wheel polishing process. First, surface 26 is polished with a 600 grit diamond wheel. Next, the polishing is continued with a 1200 grit diamond wheel. The two initial stages are then followed by two final fine-polishing steps. First, a 14,000 grit diamond wheel is used and then the process is completed on a 50,000 grit diamond wheel until a 25 nanometer rms roughness is attained.

Following each polishing stage, surface 26 is thoroughly rinsed in rubbing alcohol to remove all diamond debris acquired from the preceding polishing wheel before beginning the subsequent finer polishing step.

The silver solder preferred for bonding neck 14 to mirror blank 10 is a 50-50 silver solder, which will withstand autoclave temperatures up to 450° C. without weakening.

The assembled mirror (FIG. 4) presents smooth surfaces that are easy to sterilize and clean. Because all components can withstand 450° C. autoclave temperatures, sterilization is very simple.

Clearly, other embodiments and modifications of our invention will occur readily to those of ordinary skill in the art in view of these teachings. Therefore, our invention is to be limited only by the following claims, which include all such embodiments and modifications when viewed in conjunction with the above specification and accompanying drawing.

We claim:

1. A mirror apparatus for the examination of the interior of small cavities, said apparatus comprising:

a handle member for gripping and positioning said apparatus;

a reflecting element for reflecting incident light, said reflecting element including a piece of non-metallic material with at least one surface having a root-mean-square (rms) roughness of less than twenty-five nanometers; and flexible neck means attached between said handle member and said reflecting element for positioning said reflecting element with respect to said handle member, said flexible neck means having sufficient rigidity to withstand a lateral force of at least 2.0 newtons on said reflecting element without deformation of said flexible neck means.

2. The mirror apparatus of claim 1 wherein said piece of non-metallic material comprises:

a piece of uniformly distributed crystalline material.

3. The mirror apparatus of claim 2 wherein said crystalline material comprises:
type C-2 tungsten-carbide.

4. The mirror apparatus of claim 3 further comprising:
silver solder means for attaching said reflecting element to said flexible neck means.

5. The mirror apparatus of claim 4 wherein said flexible neck means comprises:
303 CRES stainless-steel alloy.

6. The mirror apparatus of claim 5 wherein said handle member comprises:
2024 T-4 aluminum alloy having an anodized coating, said coating having one of several colors selected according to a predetermined usage category for said mirror apparatus.

7. The mirror apparatus of claim 1 wherein said handle member comprises:
a metallic alloy.

8. The mirror apparatus of claim 7 wherein said handle member comprises:
an aluminum alloy.

9. The mirror apparatus of claim 8 wherein said handle member comprises:
2024 T-4 aluminum alloy.

10. The mirror apparatus of claim 9 wherein said handle member comprises:
an anodized coating having a selectable color for use in identifying said apparatus according to one of several predetermined categories.

11. The mirror apparatus of claim 1 wherein said flexible neck means comprises:
a monolithic piece of flexible material.

12. The mirror apparatus of claim 11 wherein said flexible neck means comprises:
a metallic alloy.

13. The mirror apparatus of claim 12 wherein said flexible neck means comprises:
303 CRES stainless-steel alloy.

14. The mirror apparatus of claim 12 wherein said handle member comprises:
2024 T-4 aluminum alloy having an anodized coating, said coating having one of several colors selected according to a predetermined usage category for said mirror apparatus.

15. A method of manufacture for a dental mirror of the type having a tungsten-carbide reflecting element with at least one reflecting element surface having a root-mean-square roughness of less than 25 nanometers, said reflecting element being bonded to a flexible neck means for adjusting the position of said reflective element, said method comprising the ordered steps of:
(a) slicing a mirror blank from a tungsten-carbide feedstock, said mirror blank having a thickness of at least 0.3 millimeters;
(b) heating said mirror blank and said flexible neck means to a temperature greater than 500° C. in the presence of silver solder such that said silver solder melts and flows over the bonding region between said mirror blank and said flexible neck means;
(c) cooling said bonding region to permit said silver solder to harden, thereby bonding said mirror blank to said flexible neck means; and
(d) polishing said mirror blank with a plurality of diamond polishing wheels until the surface roughness of said mirror blank is reduced to less than 25 nanometers rms.

16. The method of manufacture of claim 15 wherein said polishing step comprises the ordered steps of:
(d.1) polishing said mirror blank a 600 grit diamond polishing wheel;
(d.2) polishing said mirror blank with a 1200 grit diamond polishing wheel;
(d.3) polishing said mirror blank with a 14,000 grit diamond polishing wheel; and
(d.4) polishing said mirror blank with a 50,000 grit diamond polishing wheel until the surface roughness is reduced to less than 25 nanometers rms.

* * * * *